United States Patent
Singer et al.

[11] Patent Number: 6,149,426
[45] Date of Patent: Nov. 21, 2000

[54] DENTAL IMPRESSION MODELING METHOD AND APPARATUS

[76] Inventors: Gary H. Singer, 511 Abbott Dr., Broomall, Pa. 19083; Neil Gottehrer, 1717 W. Chester Pike, Havertown, Pa. 19083

[21] Appl. No.: 09/206,731

[22] Filed: Dec. 7, 1998

[51] Int. Cl.$^7$ .................................................. A61C 9/00
[52] U.S. Cl. .............................................. 433/37; 433/47
[58] Field of Search .................................. 433/37, 38, 39, 433/41, 45, 47, 214

[56] References Cited

U.S. PATENT DOCUMENTS

| | | |
|---|---|---|
| 55,465 | 6/1866 | Buttles . |
| 4,368,040 | 1/1983 | Weissman ................................. 433/36 |
| 4,375,965 | 3/1983 | Weissman ................................. 433/37 |
| 4,763,791 | 8/1988 | Halverson et al. ..................... 206/570 |
| 4,768,951 | 9/1988 | Abiru et al. ............................. 433/48 |
| 4,867,682 | 9/1989 | Hammesfahr et al. ................... 433/37 |
| 5,562,449 | 10/1996 | Jacobs et al. ........................... 433/215 |
| 5,616,027 | 4/1997 | Jacobs et al. ............................ 433/37 |
| 5,702,250 | 12/1997 | Kipke ...................................... 433/37 |
| 5,718,577 | 2/1998 | Oxman ..................................... 433/37 |
| 5,938,445 | 8/1999 | Kodama .................................... 433/37 |

*Primary Examiner*—Ralph A. Lewis
*Attorney, Agent, or Firm*—LaMorte & Associates P.C.

[57] ABSTRACT

An apparatus and associated method for accurately producing an accurate impression of a patient's teeth. The apparatus includes an improved impression tray assembly that more accurately models the teeth. The impression tray includes a segment of curable material having a top edge, a bottom edge, a face surface and a rear surface, wherein the face surface and the rear surface extend between the top edge and the bottom edge. The impression tray also includes a base plate having a peripheral edge and a groove disposed in the base plate proximate a section of the peripheral edge. The groove is adapted to receive the bottom edge of segment of curable material, thereby supporting the segment of curable material as a vertical wall. The combination of the base plate and the vertical wall of curable material produces an impression tray. The impression tray is filled with impression material and placed in the mouth. As a patient bites into the impression material, the vertical wall curable material can be molded to the contours of the teeth and gums. Once cured, the impression tray and impression material create a highly accurate impression that can be used to better model prosthetics.

16 Claims, 3 Drawing Sheets

DENTAL IMPRESSION MODELING METHOD AND APPARATUS

BACKGROUND OF THE INVENTION

1. Field of the Invention

In general, the present invention relates to impression trays and similar devices that are used to create dental models. More specifically, the present invention relates to dental modeling methods and devices that use light curable material within the mouth to create dental impressions.

2. Description of the Prior Art

When a patient is having dental work that requires teeth to be replaced, capped, covered with a bridge, or otherwise reformed with a prosthesis, it is the job of the dental practitioner to replace the involved teeth with a prosthesis that is both aesthetically pleasing and bio-mechanically correct. In the past, if a patient were to have teeth replaced or reformed, the dental practioner would produce a study model of the patient's teeth before the involved teeth were ground, removed or otherwise prepared. Similarly, the dental practioner would also model the patient's mouth after the involved teeth were prepared. Both models were then used to create a master cast from which the needed prosthesis could be formed. Due to the variables involved in preparing models using prior art methods, the initial master cast could be less than accurate. Prosthetics developed from the master cast therefore often did not properly fit and either the master cast or the prosthesis had to be repeatedly corrected. As a result, the fitting of a proper prosthesis often was obtained by trial and error, wherein the prosthetic had to be fitted and corrected numerous times before it became accurate.

One of the more common errors that occur in prior art dental modeling schemes is the inaccurate registration of the centric occlusion and vertical dimension of the involved teeth. Such inaccuracies are transferred to the prosthesis and create interdigitation misalignments in the mouth once the prosthesis is set into place. As such, the prosthesis must either be replaced or reformed to ensure a proper bite.

One of the contributing factors that leads to inaccurate models is that dentists do not always take accurate impressions. In the prior art, impressions are most commonly made using a plastic impression tray that is filled with an impression material. The impression tray is placed into the mouth and the patient bites into the impression material supported by the tray. However, impression trays only come in a few different sizes. The mouths of patients come in an infinite variety of shapes and sizes. Accordingly, available impression trays do not always properly fit in a patient mouth. The result is an incomplete or inaccurate impression that produces flawed models.

In an attempt to improve the accuracy of taking a dental impression, prior art systems have been developed where the impression material can be manipulated within the mouth by the dentist to ensure proper positioning. Once the impression material is properly positioned, the material is cured in place within the mouth. Such prior art dental impression systems are exemplified by U.S. Pat. No. 5,616,027 to Jacobs, entitled Custom Dental Tray and U.S. Pat. No. 4,867,682 to Hammesfahr, entitled Dental Impression Tray.

A problem associated with such prior art dental impression systems is that the impression tray creates a barrier around the impression material that prevents a dentist from either viewing or manipulating a large percentage of the impression material. Accordingly, if the impression material were not to properly form around a tooth in a specific area under the impression plate, the dentist would not be able to notice or correct the defect until the impression material were cured and removed. Depending upon the degree of the defect, the impression would then have to be corrected or retaken.

A need therefore exists in the art for an dental impression system that does not obstruct a dentist's access to the impression material supported by that tray. In such a manner, a dentist can view how the impression material is covering the teeth before the impression material is cured and removed.

A need also exists in the art for a dental impression modeling method and apparatus that greatly reduces the complexity of accurately creating a proper dental impression.

These needs are met by the apparatus and method as described and claimed below.

SUMMARY OF THE INVENTION

The present invention is an apparatus and associated method for accurately producing an accurate impression of a patient's teeth. The apparatus includes an improved impression tray assembly that more accurately models the teeth. The impression tray includes a segment of curable material having a top edge, a bottom edge, a face surface and a rear surface, wherein the face surface and the rear surface extend between the top edge and the bottom edge. The impression tray also includes a base plate having a peripheral edge and a groove disposed in the base plate proximate a section of the peripheral edge. The groove is adapted to receive the bottom edge of segment of curable material, thereby supporting the segment of curable material as a vertical wall. The combination of the base plate and the vertical wall of curable material produces an impression tray. The impression tray is filled with impression material and placed in the mouth. As a patient bites into the impression material, the vertical wall curable material can be molded to the contours of the teeth and gums. Once cured, the impression tray and impression material create a highly accurate impression that can be used to better model prosthetics.

BRIEF DESCRIPTION OF THE DRAWINGS

For a better understanding of the present invention, reference is made to the following description of two exemplary embodiments thereof, considered in conjunction with the accompanying drawings, in which.

DETAILED DESCRIPTION OF AN EXEMPLARY EMBODIMENT

Although the present invention apparatus and method can be used to make an accurate model of the mouth for many different purposes, the present invention is particularly well suited for producing an accurate model of the mouth for use in the creation of dental prosthetics. Accordingly, the present invention apparatus and method will be described in a common application where an impression is needed to prepare the dental model required to produce a prothesis.

Figure 1:
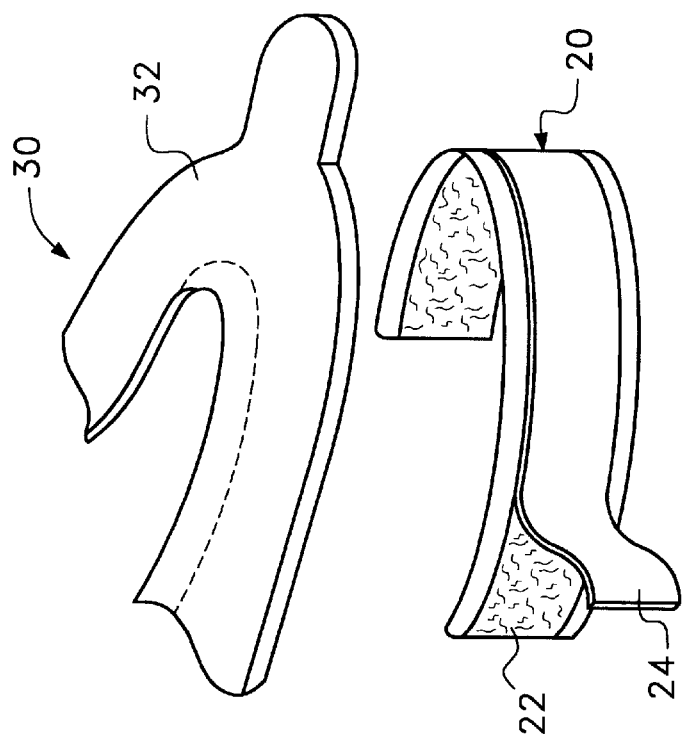
FIG. 1 is an exploded, perspective view of one embodiment of a maxillary impression tray assembly used in accordance with the present invention. The impression tray assembly is shown in conjunction with a mouth that has the lips selectively cut away to clearly illustrate the teeth.
Figure 1:
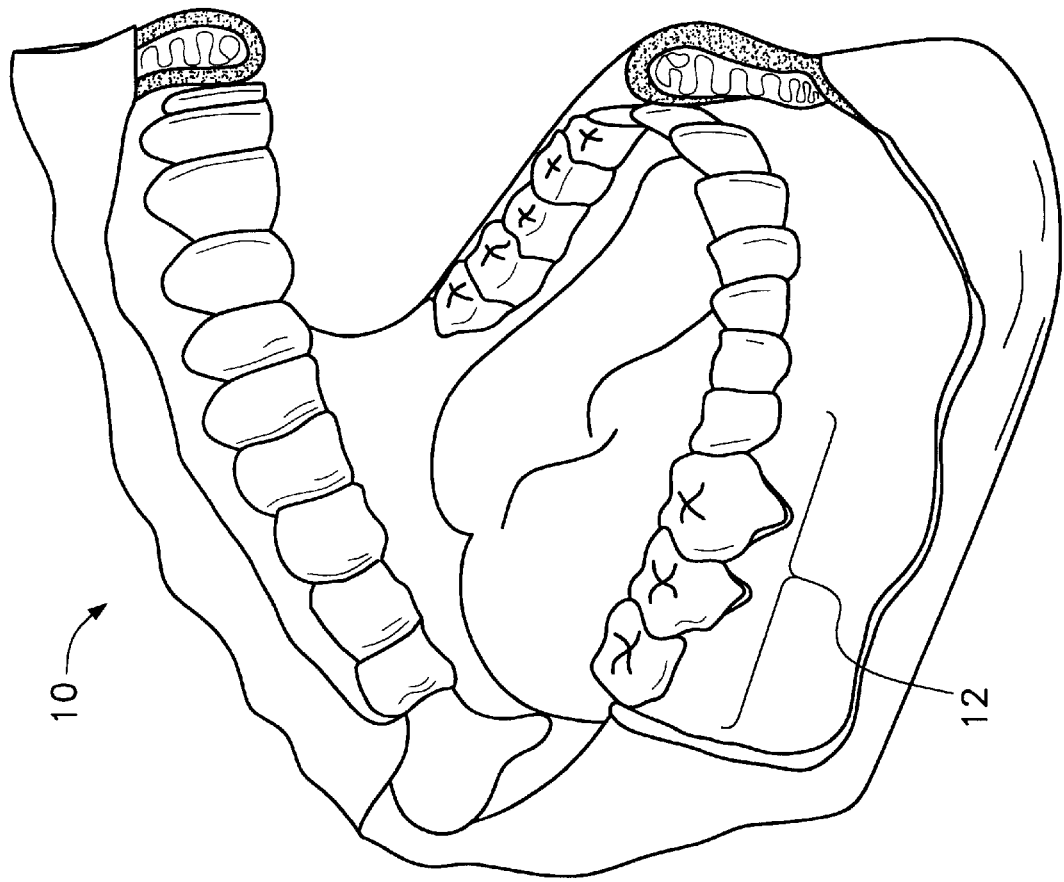

Referring to FIG. 1, a maxillary arch dental impression tray apparatus 10 is shown in accordance with the present invention. The dental impression tray apparatus 10 includes a base plate 12. The base plate 12 has a semi-oval shape and a palate contour typical of other impression trays. However, the base plate 12 does not contain the traditional vertical wall that extends upwardly from many prior art impression trays. Rather the peripheral edge of the base plate 12 is generally no thicker than any other part of the base plate 12.

An optional holding tab 14 can extend from the base plate 12 to assist the dentist manipulate the base plate 12 within the mouth. The base plate 12 and the holding tab 14 can be made of any material traditionally associated with impression trays. However, in the preferred embodiment, both the holding tab 14 and the base plate 12 are made of stainless steel or some other material that can be sterilized in an autoclave.

A groove 16 is disposed in the top surface of the base plate 12. The groove 16 follows the periphery of the base plate 12 along its semi-oval shape. The groove 16 is shaped to receive the bottom edge 18 of a moldable vertical wall assembly 20. The moldable vertical wall assembly 20 contains an elongated segment of curable polymer material 22. The elongated segment of curable material 22 can be any air curable material, water curable material or temperature curable material used in the field of dental impressions. However, in the preferred embodiment, the elongated segment of curable material 22 is a light curable material such as the polymer Triad™, which is manufactured by Dentsply International of York, Pa.

The elongated segment of curable material 22 is covered on at least one side by a protective strip of waxed paper or an equivalent protective strip 24. The protective strip 24 protects the segment of curable material 22 from contamination and allows different segments of curable material 22 to be stored against each other without contact. The protective strip 24 is made to a gauge thickness that is adequate enough to provide a degree of rigidity to the curable material. The rigidity provided by the strip of waxed paper is preferably enough to prevent the segment of curable material 22 from folding under its own weight when it is supported along one of its long edges. In other words, the protective strip 24 enables the segment of curable material 22 to stand upright without folding over when resting along its bottom edge 18.

The moldable vertical wall assembly 20 may also include an optional rim element 26 that covers the top edge of the segment of curable material 22. The rim element 26 provides longitudinal rigidity to the segment of curable material 22 yet enables the segment of curable material 22 to bend. Although the rim element 26 can be plastic, it is preferably made of malleable metal so that it can be bent into a shape that matches the semi-oval shape of the groove 16 in the below lying base plate 12.

To use the maxillary arch dental impression tray assembly 10, a base plate 12 is selected that is appropriate for the size of the patient's mouth. The moldable vertical wall assembly 20 is then attached to the base plate 12 by manually pressing the bottom edge 18 of the segment of curable material 20 into the groove on the base plate 12. The segment of curable material 22 therefore creates a vertical wall that extends upwardly from the base plate 12 along the periphery of the base plate 12. The segment of curable material 22 is supported by the protective strip 24 which prevents the segment of curable material 22 from folding under its own weight. After the moldable vertical wall assembly 20 is applied to the base plate 12, the area above the base plate 12 and within the moldable vertical wall assembly 20 is filled with a conventional impression material. The impression material can be heat curable, light curable, air curable or water curable.

Figure 2:
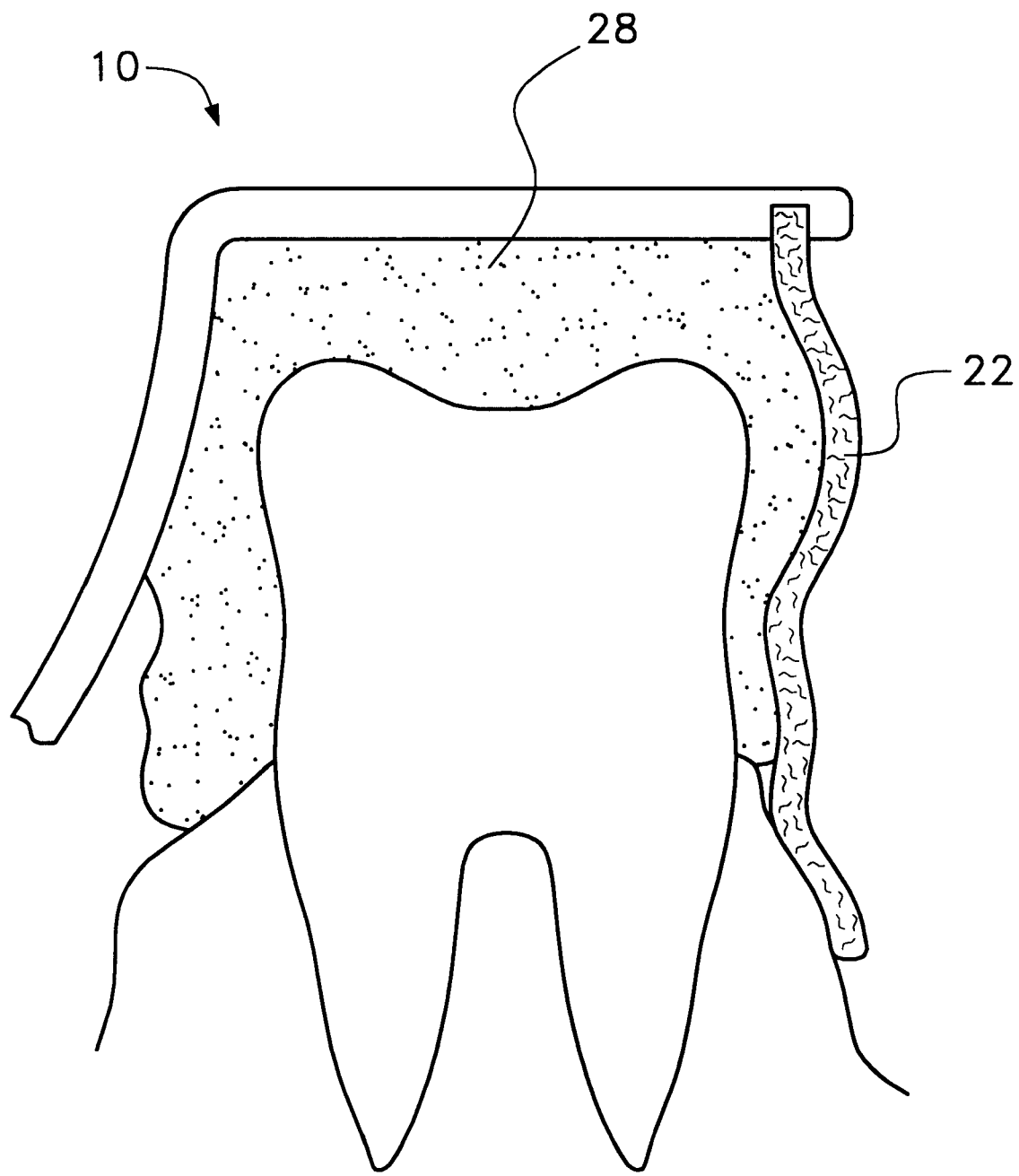
FIG. 2 is a cross-sectional view of the embodiment of FIG. 1 shown applied over a tooth.

Referring to FIG. 2, it can be seen that once the maxillary arch dental impression tray assembly 10 is filled with impression material 28, the impression tray assembly 10 is placed within the mouth and is pressed against the maxillary arch. Once in place, a dentist can then manually press the segment of curable material 22 against the teeth and gums of the maxillary arch. By pressing the segment of curable material 22, the segment of curable material 22 conforms to the shape of both the teeth and gums while simultaneously causing the impression material 28 behind the wall of curable material to conform to the contours of the teeth and gums. Once the maxillary arch impression tray assembly 10 is in place and the wall of curable material is manipulated and seated, the wall of curable material 22 and the impression material 28 can be caused to cure. After curing, the maxillary arch impression tray assembly 10 is removed and a very high quality impression is obtained.

Figure 3:
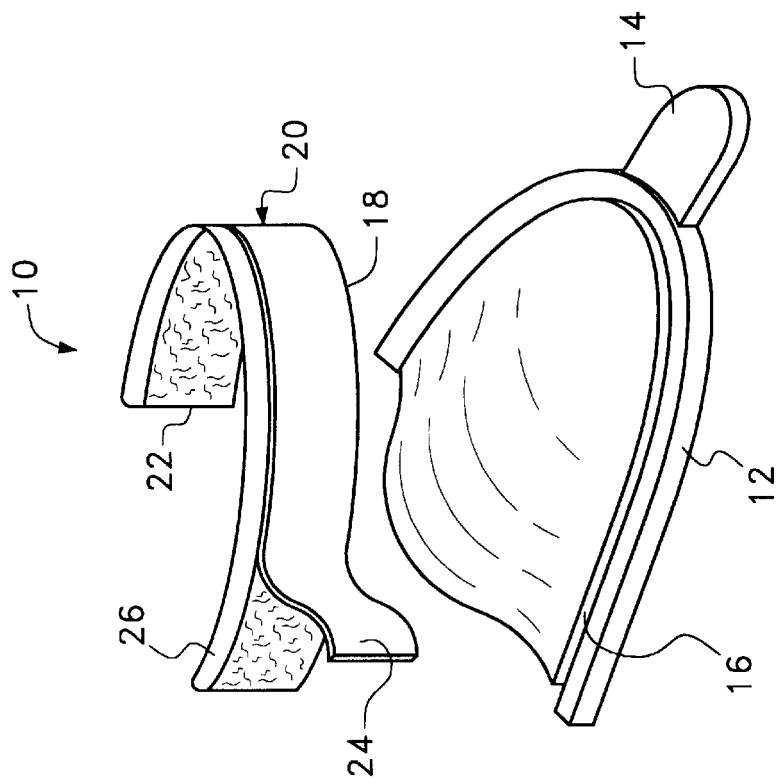
FIG. 3 is an exploded, perspective view of one embodiment of a mandibular impression tray assembly used in accordance with the present invention. The impression tray assembly is also shown in conjunction with a mouth that has the lips selectively cut away to clearly illustrate the teeth.
Figure 3:
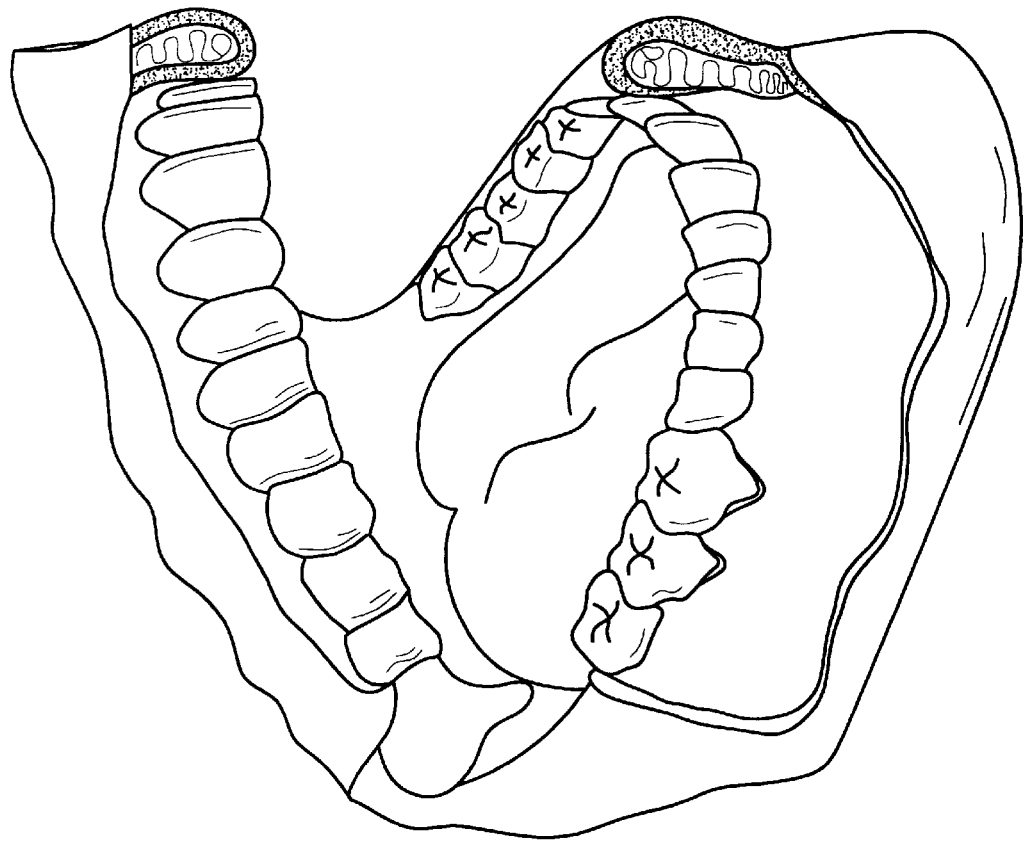

Referring to FIG. 3, a mandibular arch dental impression tray assembly 30 is shown in accordance with the present invention. The mandibular dental impression tray assembly also includes a base plate 32. The base plate 32 is semi-oval in shape and defines a central relief for movement of the tongue. A groove (not shown) is present in the base plate 32 proximate its peripheral edge.

The groove in the base plate 32 is adapted to receive a moldable vertical wall assembly 20 that is identical to the type previously described. The base plate 32 receives the moldable vertical wall assembly 20 in the same manner as was previously described. As such, it should be understood that identical moldable vertical wall assemblies 20 can be used in either the mandibular arch impression tray assembly 10 (FIG. 1) or the maxillary arch impression tray assembly 30. Once the moldable vertical wall assembly 20 is affixed to the mandibular base plate 32, the segment of curable material 22 in the moldable vertical wall assembly 20 creates the vertical wall of the mandibular arch impression tray assembly 30.

To use the mandibular arch dental impression tray assembly 10, a base plate 32 is selected that is appropriate for the size of the patient's mouth. After the moldable vertical wall assembly 20 is applied to the base plate 32, the area defined by the base plate 32 and the moldable vertical wall assembly 20 is filled with a conventional impression material. The impression material can be heat curable, light curable, air curable or water curable.

Once filled with impression material, the mandibular arch dental impression tray assembly 30 placed within the mouth and the protective cover 24 is removed. Once in place, a dentist can then manually press the segment of curable material 22 against the teeth and gums of the mandibular arch. By manipulating the segment of curable material 22, the curable material 22 conforms to the shape of both the teeth and gums while simultaneously causing the impression material behind the wall of curable material to conform to the contours of the teeth and gums. Once the mandibular arch impression tray assembly 30 is in place and the segment of curable material 22 is manipulated and seated, the segment of curable material 22 and the impression material can be caused to cure. After curing, the mandibular arch impression tray assembly 30 is removed and a very high quality impression is obtained.

It will be understood that the specifics of the apparatus and method described are merely exemplary and that the present invention can be practiced using functionally equivalent components and/or method steps. All such modifications and alternate embodiments that are obvious to a person skilled in the art are intended to be included within the scope of the present invention as defined by the below appended claims.

What is claimed is:

1. An impression tray assembly, comprising:
    a segment of curable material having a top edge, a bottom edge, a face surface and a rear surface, wherein said face surface and said rear surface extend between said top edge and said bottom edge;
    a removable strip of protective material covering said face surface of said segment of curable material; and
    a base plate having a peripheral edge and a groove disposed in said base plate proximate a section of said peripheral edge, wherein said groove is adapted to receive said bottom edge of segment of curable material.

2. The assembly according to claim 1, wherein said strip of material is of a thickness great enough to support said segment of curable material so that said top edge of said segment of curable material does not fold over when said bottom edge of said segment of material is engaged within said groove.

3. The assembly according to claim 1, wherein said base plate is metal.

4. The assembly according to claim 1, further including a bendable rim element disposed along said top edge of said segment of curable material.

5. The assembly according to claim 4, wherein said bendable rim element is metal.

6. The assembly according to claim 1, wherein said segment of curable material is selected from a group consisting of heat curable material, light curable material, air curable material and water curable material.

7. An impression tray assembly, comprising:
    a base plate;
    a vertical wall extending upwardly from said base plate, wherein said vertical wall contains curable material in an uncured state, thereby enabling said vertical wall to be manually molded against different contours of the teeth within the mouth; and
    at least one removable protective strip that covers a surface of said vertical wall, thereby protecting said surface from contact contamination.

8. The assembly according to claim 7, wherein said vertical wall is selectively attachable and detachable from said base plate.

9. The assembly according to claim 7, wherein said vertical wall has a top edge and said assembly further includes a bendable rim element disposed along said top edge of said vertical wall.

10. The assembly according to claim 9, wherein said bendable rim element is metal.

11. The assembly according to claim 7, wherein said base plate is metal.

12. The assembly according to claim 7, wherein said base plate has a peripheral edge and a groove disposed in said base plate proximate a section of said peripheral edge, wherein said groove is adapted to receive a bottom edge of segment of curable material.

13. An impression tray assembly, comprising:
    a segment of curable material having a top edge, a bottom edge, a face surface and a rear surface, wherein said face surface and said rear surface extend between said top edge and said bottom edge;
    a bendable metal rim element disposed along said top edge of said segment of curable material; and
    a base plate having a peripheral edge and a groove disposed in said base plate proximate a section of said peripheral edge, wherein said groove is adapted to receive said bottom edge of segment of curable material.

14. The assembly according to claim 13, further including a removable strip of protective material covering said face surface of said segment of curable material.

15. The assembly according to claim 14, wherein said strip of material is of a thickness great enough to support said segment of curable material so that said top edge of said segment of curable material does not fold over when said bottom edge of said segment of material is engaged within said groove.

16. The assembly according to claim 10, wherein said base plate is metal.

* * * * *